(12) United States Patent
Chou

(10) Patent No.: US 11,766,517 B2
(45) Date of Patent: Sep. 26, 2023

(54) INSERT-STORAGE TYPE INTRAVENOUS DRIP MOVING SEAT

(71) Applicant: BETTER ENTERPRISE CO., LTD., Taipei (TW)

(72) Inventor: Cheng-Yi Chou, Taipei (TW)

(73) Assignee: BETTER ENTERPRISE CO., LTD., Taipei (TW)

( * ) Notice: Subject to any disclaimer, the term of this patent is extended or adjusted under 35 U.S.C. 154(b) by 449 days.

(21) Appl. No.: 17/204,913

(22) Filed: Mar. 17, 2021

(65) Prior Publication Data
US 2022/0296807 A1 Sep. 22, 2022

(51) Int. Cl.
*A61M 5/00* (2006.01)
*A61M 5/14* (2006.01)
*F16M 11/42* (2006.01)

(52) U.S. Cl.
CPC .......... *A61M 5/1415* (2013.01); *F16M 11/42* (2013.01); *A61M 2209/08* (2013.01)

(58) Field of Classification Search
CPC .. A61M 5/00; A61M 5/1415; A61M 2209/08; F16M 11/42
USPC ...................................... 280/79.11
See application file for complete search history.

(56) References Cited

U.S. PATENT DOCUMENTS

| | | | |
|---|---|---|---|
| D657,470 S * | 4/2012 | Schon | D24/186 |
| 8,196,874 B2 * | 6/2012 | Zitting | F16M 11/42 |
| | | | 248/129 |
| 8,286,977 B2 * | 10/2012 | Butler | A61B 50/10 |
| | | | 280/47.35 |
| 8,684,375 B2 * | 4/2014 | Fink | B60B 33/0026 |
| | | | 248/129 |
| D722,696 S * | 2/2015 | Blomquist | D24/164 |
| 9,370,617 B2 * | 6/2016 | Chepurny | B60B 33/0089 |
| 10,060,571 B2 * | 8/2018 | Koehler | F16M 11/42 |
| 10,238,792 B1 * | 3/2019 | Macri | F16M 11/42 |
| 10,369,273 B2 * | 8/2019 | Koehler | A61M 5/1415 |
| D936,839 S * | 11/2021 | Couch | D24/185 |
| 2013/0228997 A1 * | 9/2013 | Fukuhara | A61M 5/1417 |
| | | | 280/304.1 |
| 2016/0114102 A1 * | 4/2016 | Yamamoto | A47B 13/003 |
| | | | 108/27 |

* cited by examiner

*Primary Examiner* — Hau V Phan
(74) *Attorney, Agent, or Firm* — Fei-hung Yang

(57) ABSTRACT

An insert-storage intravenous drip moving seat includes a main body, two extension support arms, an inverted V-shaped support arm and plural moving wheels. The two extension support arms form a V-shaped structure, and each is bent and connected to a fixed bar, so that a storage space is formed under the main body and the two extension support arms; the bottom of both ends of each fixed bar has a moving wheel; the inverted V-shaped support arm is connected to the two extension support arms; the bottom of the other ends of the inverted V-shaped support arm has one of the moving wheels; both moving wheels are disposed on the same radius distance; and a guide entrance is formed between the two fixed bars and corresponsive to the inverted V-shaped support arm to provide an insert-storage design of the inverted V-shaped arm by the guide entrance.

6 Claims, 5 Drawing Sheets

INSERT-STORAGE TYPE INTRAVENOUS DRIP MOVING SEAT

BACKGROUND

Technical Field

This disclosure relates to the field of medical supplies, in particular to an intravenous drip moving seat for installing a drip stand to provide a mobile feature, and the intravenous drip moving seat of this disclosure can be stored by an insert-storage method while taking the strength of usage into account by means of a special one-piece structural design to reduce the volume and footprint of the intravenous drip moving seat.

Description of the Related Art

Intravenous injection is a common medical measure that places a needle on a patient's body, connects the needle to a bottle or a bag of medical liquid such as blood, medicinal liquid, nutrient liquid, etc. and transfers the medical liquid to the needle through a tube and finally into the patient's body. This medical measure is intended for controlling the injection volume and injecting the medical liquid into the patient's body continuously for a long time. The bottle or bag of medical liquid must be hung at a position higher than the needle. In general, the bottle or bag is hung on a side of the patient, thus ending up with a variety of drip stands of different functions, such as a mobile drip stand that can be pushed and moved, a fixed drip stand nailed and fixed to a wall, a wearable drip stand directly worn on the patient's body or other fixed drip stands fixed on a wheelchair, a walker, a hospital bed, etc. For example, the mobile drip stand is provided for hanging the bottle or bag of medical liquid and facilitating moving, and this stand usually comes with a height adjusting function based on the patient's using requirements, and the stand is usually installed vertically at the center of the intravenous drip moving seat, so that the patient can go to different places for taking a medical checkup or a walk for relaxation while having the intravenous injection, so as to prevent the infusion from being disturbed. However, these mobile drip stands are generally moved close to one another for storage, and the design of the intravenous drip moving seats will cause the moving seats to interfere with one another and lead to a large occupied area, and sometimes the moving seats may hook one another and lead to an inconvenient access. In addition, an operator of the mobile drip stand including a patient or a healthcare worker has more or less experience of being tripped by the mobile drip stand, kicking the mobile drip stand accidentally, or falling down due to an unstable center of gravity. In the design of these intravenous drip moving seats, the bottom of the moving seats is provided with a plurality of moving wheels to form a multi-point support moving plane in order to improve the stability of moving or stopping the moving stands. Most of the moving stands are arranged radially outward by using the stand as the center, so that the moving wheels can evenly share the weight of the stand, and the moving wheels are evenly dispersed on the same radius distance of the center of the intravenous drip moving seat. To reduce weight and volume, a structural design with five claw-support feet is often adopted. However, these claw-support feet will jam one another during storage due to the extending directions of the support feet, thus resulting in a very small part of overlap of the storage space and failing to reduce the storage volume effectively. Relatively speaking, the intravenous drip moving seats still occupy a considerable footprint after storage. Obviously, the conventional intravenous drive moving seats require improvements.

In view of the aforementioned drawbacks of the prior art, the discloser of this disclosure based on years of experience in the related industry to conduct extensive research and experiment on the physical characteristics of the mobile drip stands for their use and storage, and finally designed and developed a sequentially insert-storage type intravenous drip moving seat that uses a main body and two extension support arms to form a guide entrance of an inverted V-shaped support arm and a storage space capable of accommodating the inverted V-shaped support arm, and further uses a spatial change and a guiding storage method for the sequential insert-storage of any two intravenous drip moving seats to achieve a larger overlap, so as to reduce the storage volume and footprint of the intravenous drip moving seats after storage.

SUMMARY

Therefore, it is a primary objective of this disclosure to provide an insert-storage intravenous drip moving seat having a main body, two extension support arms, an inverted V-shaped support arm and a plurality of moving wheels. After precise computations, a guide entrance is formed between the main body and two extension support arms for passing and receiving the inverted V-shaped support arm and a storage space is formed for accommodating the inverted V-shaped support arm. During storage, the inverted V-shaped support arm of one of the intravenous drip moving seats is passed through the guide entrance and placed into the storage space of the front intravenous drip moving seat and the two extension support arms of the front intravenous drip moving seat are engaged with the two extension support arms of the rear intravenous drip moving seat, so that the intravenous drip moving seats 1 can be insert-stored sequentially according to the aforementioned method to achieve the effect of reducing storage volume and footprint significantly after storage.

To achieve the aforementioned and other objectives, this disclosure discloses an insert-storage intravenous drip moving seat manufactured by an integral formation method and provided for installing required moving objects, comprising: a main body, having an assembling portion disposed at the middle thereof; two extension support arms, each having an arm body and a fixed bar, and each of the arm bodies having an end coupled to the main body and the other end downwardly bent, extended, and coupled onto the fixed bar, and a storage space being defined under the main body and the two extension support arms, and a first fixed portion being disposed separately under both ends of each of the fixed bars, and the two extension support arms extending into a V-shaped by using the main body as a center, and the first fixed portions being disposed on the same radius distance by using the main body as a center, so that the two fixed bars are limited by a relative positional relationship of the first fixed portions to show the same V-shaped angle, and a guide entrance is formed between the two fixed bars; an inverted V-shaped support arm, with two open ends coupled to the arm bodies of the two extension support arms respectively, and one closed end extending downwardly and forwardly to form a tip, and a second fixed portion being disposed under the tip and also disposed on the same radius distance where the first fixed portions are situated, and the inverted V-shaped support arm having a width smaller than the width of the guide entrance; and a plurality of moving wheels, respectively and movably installed to the first fixed portions and the second fixed portions, so that each of the moving wheels can be rotated relative to one of the first fixed portions and/or one of the second fixed portions, and each of the moving wheels can rotate on its own and drive the intravenous drip moving seat to move in any direction on a plane.

In an embodiment of this disclosure, the first fixed portions and the second fixed portion are arranged equidistantly on the same radius distance of the main body to stabilize the movement and share the weight exerted by an object. It should be noted that the first fixed portions and the second fixed portion may also be arranged non-equidistantly on the same radius distance of the main body 11 as long as balance can be maintained.

In another embodiment of this disclosure, the main body, the extension support arms and the inverted V-shaped support arm have a bottom with a hollow design to reduce weight, and a plurality of reinforcing ribs disposed at the bottom of the main body, the extension support arms and the inverted V-shaped support arm to increase strength. In addition, the reinforcing ribs at the bottom of the extension support arms and the inverted V-shaped support arm are staggered and crisscrossed to form a plurality of intersections, and a portion of the intersections have a plurality of third fixed portions provided for installing at least one counterweight, or the reinforcing ribs at the bottom of the main body, the first fixed portions and the second fixed portion are configured to be radiated outwardly.

BRIEF DESCRIPTION OF THE DRAWINGS

This disclosure will become clearer in light of the following detailed description of an illustrative embodiment of this disclosure described in connection with the drawings.

DESCRIPTION OF THE EMBODIMENTS

Figure 1:
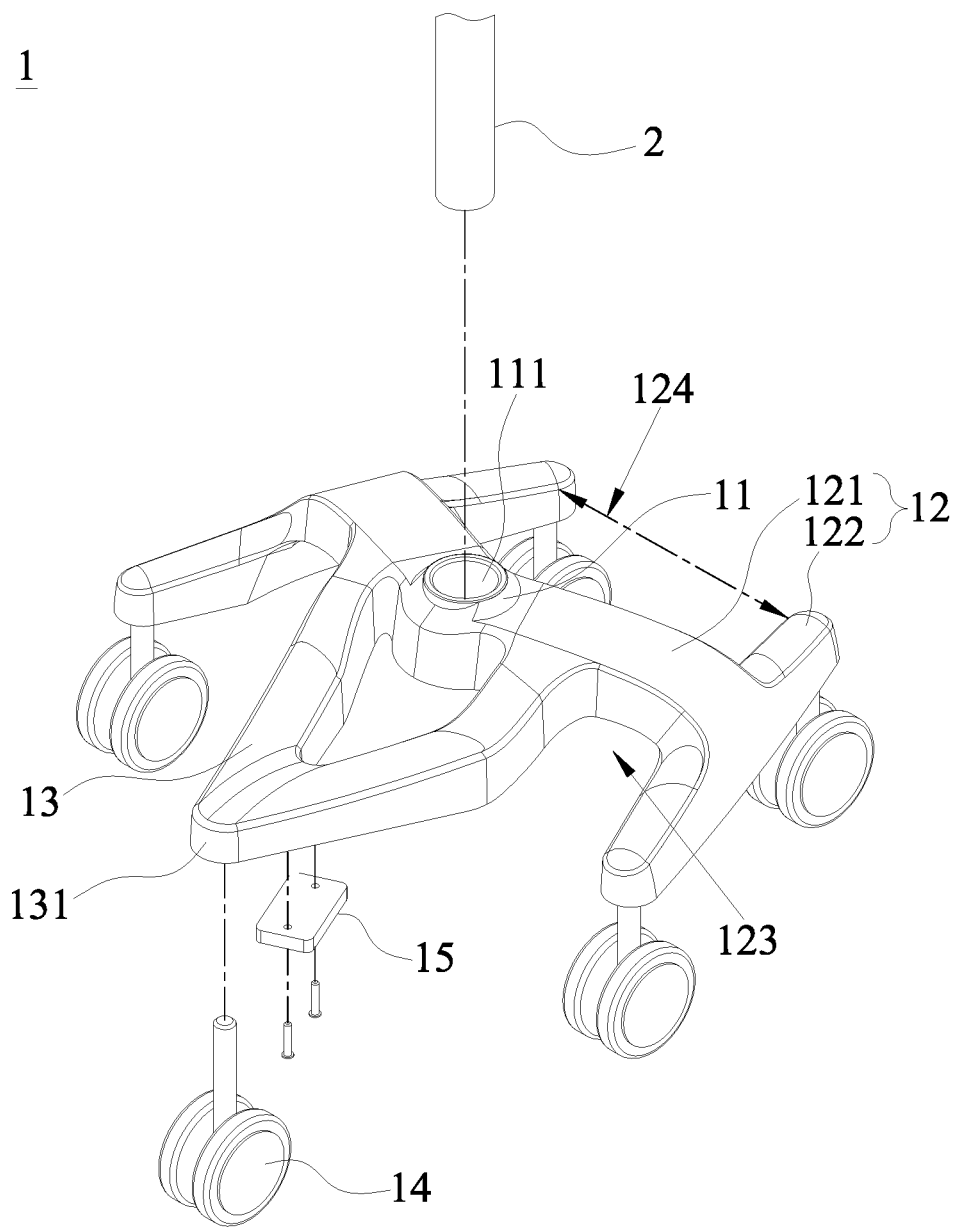
FIG. 1 is a first schematic view of a preferred embodiment of this disclosure.
Figure 2:
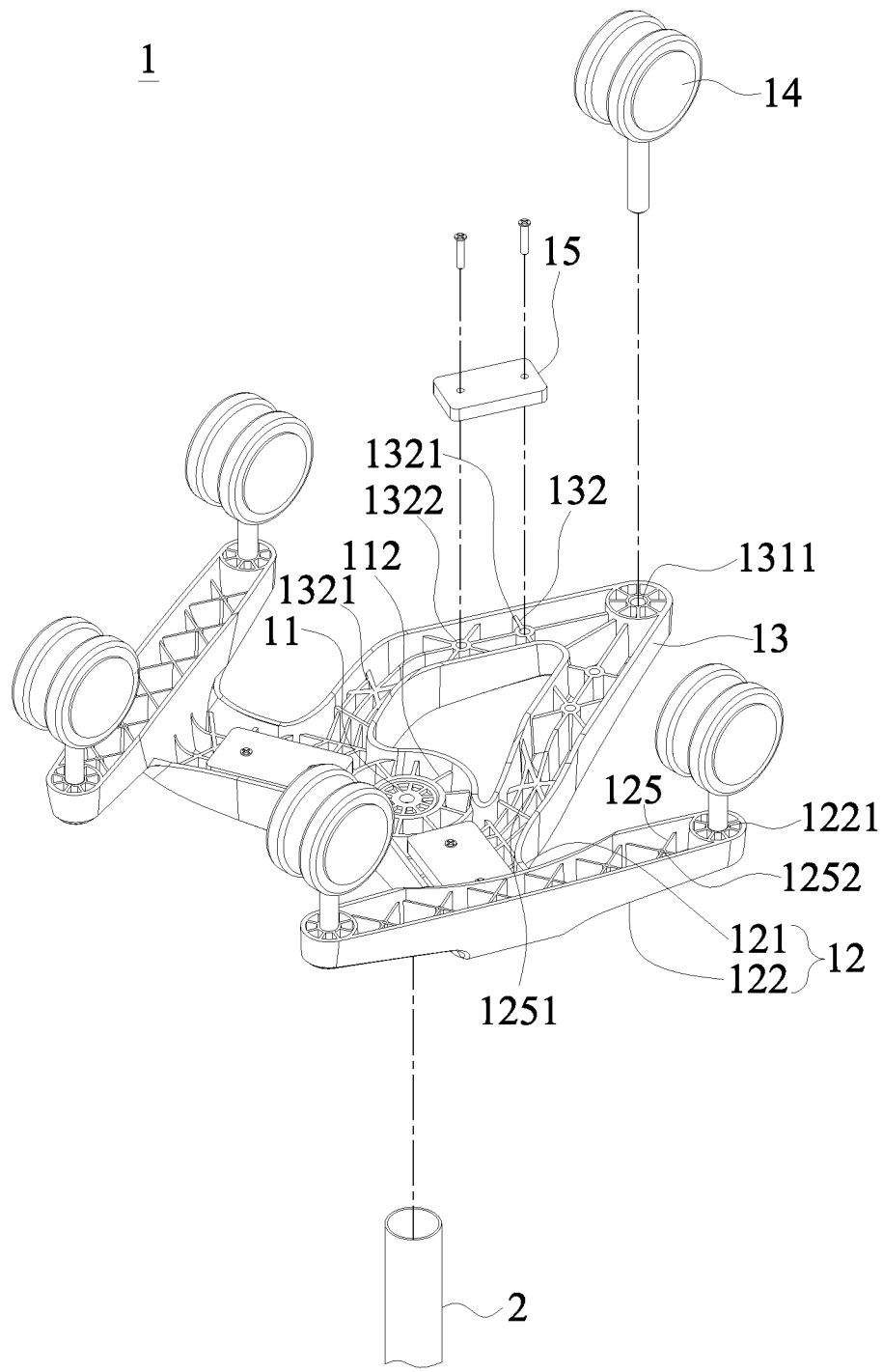
FIG. 2 is a second schematic view of a preferred embodiment of this disclosure.
Figure 3:
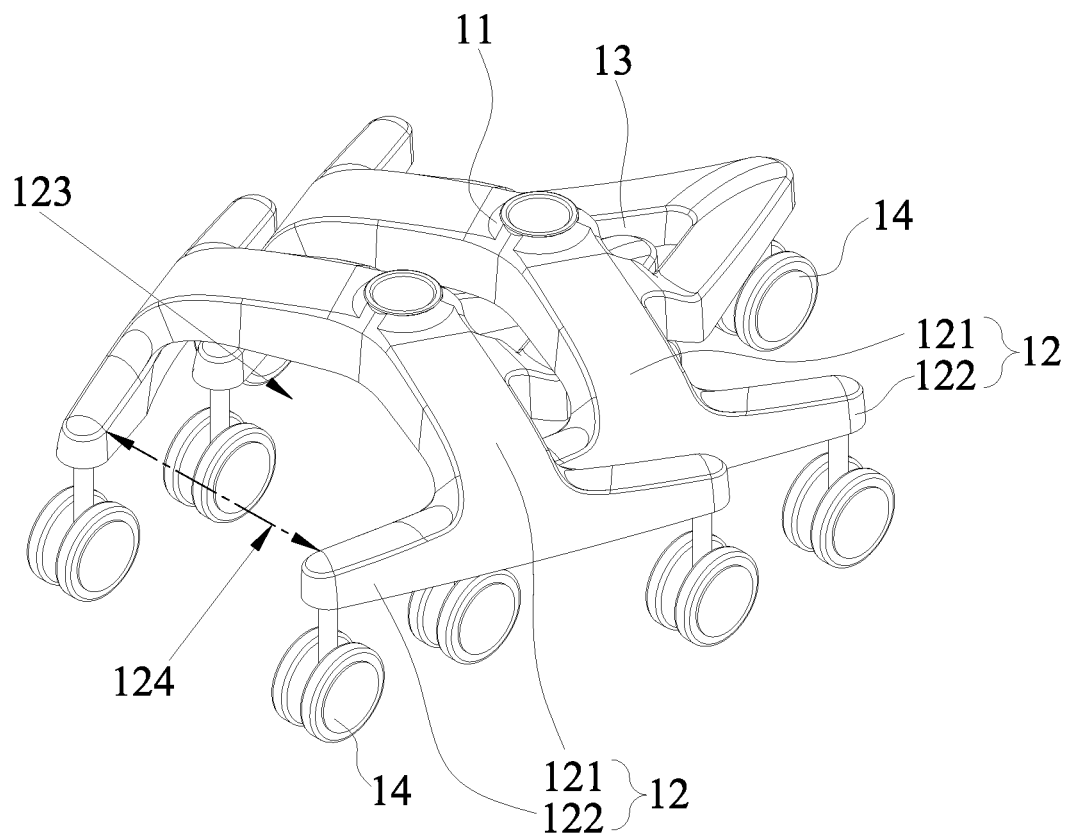
FIG. 3 is a first schematic view of a preferred embodiment of this disclosure in a state of performing an insert-storage.
Figure 4:
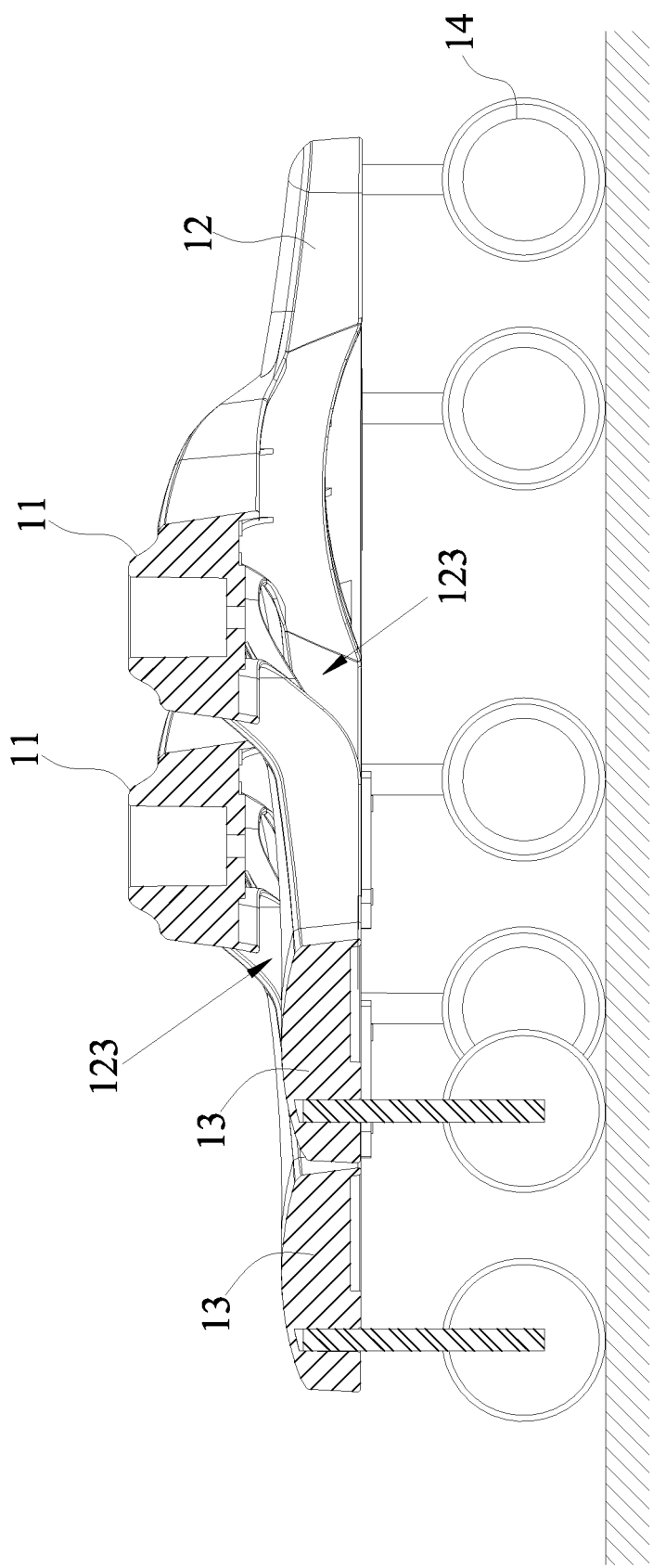
FIG. 4 is a second schematic view of a preferred embodiment of this disclosure in a state of performing an insert-storage.

Exemplary embodiments are illustrated in reference with the drawings. It is intended that the embodiments and figures disclosed herein are to be considered illustrative rather than restrictive.

With reference to FIGS. 1, 2 and 3-5 for the schematic views of a preferred embodiment of this disclosure viewing from different angles, the schematic views of different insert-storage statuses, and the bottom view of an insert-storage intravenous drip moving seat 1 in accordance with a preferred embodiment of this disclosure respectively, the insert-storage intravenous drip moving seat 1 is manufactured by an integral formation method and provided for installing a required moving object 2, and the insert-storage intravenous drip moving seat 1 includes a main body 11, two extension support arms 12, an inverted V-shaped support arm 13 and a plurality of moving wheels 14.

Wherein, the center of the main body 11 has an assembling portion 111 designed with a shape of a circular hole and provided for passing the object 2 in a shape of a round rod. It should be noted that the object 2 can be either a seat body or a drip stand, which is installed by inserting the round rod into the assembling portion 111.

Figure 5:
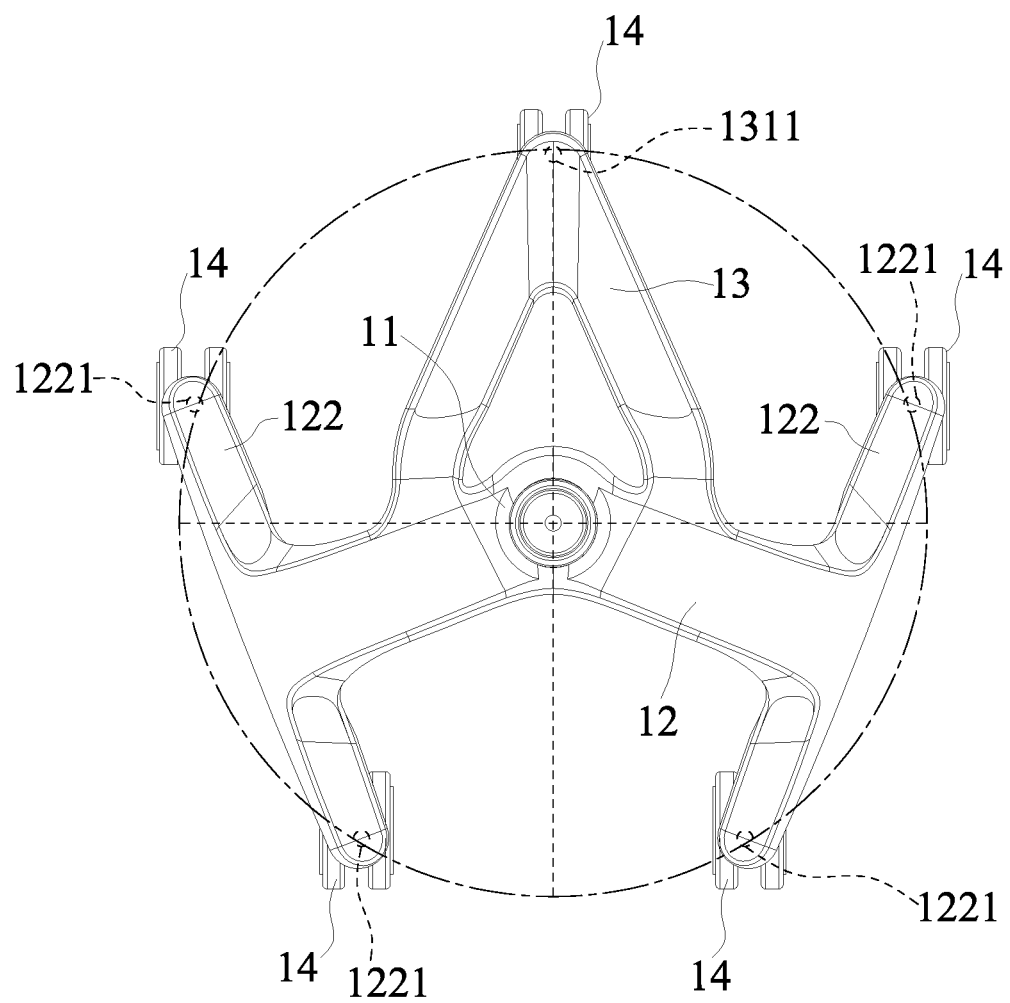
FIG. 5 is a bottom view of a preferred embodiment of this disclosure.

Each of the extension support arms 12 has an arm body 121 and a fixed bar 122, and each of the arm bodies 121 has an end connected to the main body 11 and the other end downwardly bent, extended, and connected to a midpoint position of the fixed bar 122, and a storage space 123 is formed under the main body 11 and the two extension support arms 12, and each of the fixed bars 122 has a first fixed portion 1221 disposed under both ends of the fixed bar 122 separately, and the two extension support arms 12 are extended into a V-shape by using the main body 11 as the center, and the radian of the included angle of the V-shape is 144 degrees. In FIG. 5, the first fixed portions 1221 are disposed on the same radius distance of the center of the main body 11, so that the two fixed bars 122 are limited by the relative positional relationship of the first fixed portions 1221 to show a V-shaped angle, and a guide entrance 124 is formed between the two fixed bars 122. In a side view, the main body 11 protrudes from the plane formed by the two fixed bars 122.

Two open ends of the inverted V-shaped support arm 13 are connected to the arm bodies 121 of the two extension support arms 12 respectively, and one closed end is extended downwardly forward to form a tip 131, and a second fixed portion 1311 is disposed under the tip 131, so that the second fixed portion 1311 is disposed on the same radius distance of the main body 11. In addition, the width of the two open ends of the inverted V-shaped support arm 13 is corresponsive to the width of the guide entrance 124. It should be noted that the tip 131 is in an A-shape or a U-shape, and the first fixed portions 1221 and the second fixed portion 1311 are arranged equidistantly on the same radius distance of the main body 11, and their radian is 72 degrees. It should be noted that the first fixed portions 1221 and the second fixed portion 1311 may also be arranged non-equidistantly on the same radius distance of the main body 11 as long as balance can be maintained.

The moving wheels 14 are respectively and movably installed to the first fixed portions 1221 and the second fixed portions 1311, so that each of the moving wheels 14 can be rotated relative to the first fixed portion 1221 and/or the second fixed portion 1311, and each of the moving wheels 14 can be rotated on its own to drive the intravenous drip moving seat 1 to move in any direction on a plane.

In addition, the bottom of the main body 11, the extension support arms 12 and the inverted V-shaped support arm 13 comes with a hollow design to reduce weight, and the bottom of the main body 11, the extension support arms 12 and the inverted V-shaped support arm 13 has a plurality of reinforcing ribs 112, 125, 132 respectively to enhance strength, and the reinforcing ribs 125, 132 at the bottom of the extension support arms 12 and the inverted V-shaped support arm 13 are staggered and crisscrossed to form a plurality of intersections 1251, 1321, and a portion of the intersection 1251, 1321 has a plurality of third fixed portions 1252 provided for installing at least one counterweight 15. In addition the reinforcing ribs 125, 132 at the bottom of the main body 11, the first fixed portions 1221 and the second fixed portion 1311 are configured to be radially outward.

Therefore, when a plurality of intravenous drip moving seats 1 are insert-stored, the inverted V-shaped support arm 13 of the intravenous drip moving seat 1 is passed through the guide entrance 123, so that the inverted V-shaped support arm 13 is placed into the storage space 123 of the front intravenous drip moving seat 1, and the two fixed bars 122 of the front intravenous drip moving seat 1 are engaged with the two fixed bars 122 of the rear intravenous drip moving seat 1, so that the intravenous drip moving seats 1 can be insert-stored according to the aforementioned method. In summation, the intravenous drip moving seat 1 of this disclosure uses the main body 11 and the two extension support arms 12 to form the guide entrance 124 for passing and receiving the inverted V-shaped support arm 13 and the storage space 123 for accommodating the inverted V-shaped support arm 13, and the spatial change is used to store the inverted V-shaped support arm 13, so that two adjacent intravenous drip moving seats 1 can be passed, inserted, and stored sequentially. The overlapped part of the storage can reduce the storage volume and make the storage more tidily and not easy to separate from one another. Obviously, this disclosure has the effect of reducing storage volume and footprint significantly after storage.

While the invention has been described by means of specific embodiments, numerous modifications and variations could be made thereto by those skilled in the art without departing from the scope and spirit of the invention set forth in the claims.

What is claimed is:

1. An insert-storage intravenous drip moving seat, manufactured by an integral formation method, and provided for installing objects that are required moving, comprising:
    a main body, having an assembling portion disposed at the middle thereof;
    two extension support arms, each having an arm body and a fixed bar, and each of the arm bodies having an end coupled to the main body and the other end downwardly bent, extended, and coupled onto the fixed bar, and a storage space being defined under the main body and the two extension support arms, and a first fixed portion being disposed separately under both ends of each of the fixed bars, and the two extension support arms extending into a V-shaped by using the main body as a center, and the first fixed portions being disposed on the same radius distance by using the main body as a center, so that the fixed bars are limited by a relative positional relationship of the first fixed portions to show the same V-shaped angle, and a guide entrance is formed between the fixed bars;
    an inverted V-shaped support arm, with two open ends coupled to the arm bodies of the two extension support arms respectively, and one closed end extending downwardly and forwardly to form a tip, and a second fixed portion being disposed under the tip and also disposed on the same radius distance where the first fixed portions are situated, and the inverted V-shaped support arm having a width smaller than the width of the guide entrance; and
    a plurality of moving wheels, respectively and movably installed to the first fixed portions and the second fixed portions, so that each of the moving wheels can be rotated relative to one of the first fixed portions and/or one of the second fixed portions, and each of the moving wheels can rotate on its own and drive the intravenous drip moving seat to move in any direction on a plane.

2. The insert-storage intravenous drip moving seat as claimed in claim 1, wherein the first fixed portions and the second fixed portions are non-equidistantly arranged on the same radius distance of the main body.

3. The insert-storage intravenous drip moving seat as claimed in claim 1, wherein the main body, the extension support arms and the inverted V-shaped support arm have a bottom with a hollow design to reduce weight, and a plurality of reinforcing ribs disposed at the bottom of the main body, the extension support arms and the inverted V-shaped support farm to enhance strength.

4. The insert-storage intravenous drip moving seat as claimed in claim 3, wherein the reinforcing ribs at the bottom of the extension support arms and the inverted V-shaped support arm are staggered and crisscrossed to form a plurality of intersections, and a portion of the intersections have a plurality of third fixed portions provided for installing at least one counterweight.

5. The insert-storage intravenous drip moving seat as claimed in claim 4, wherein the reinforcing ribs at the bottom of the main body, the first fixed portions and the second fixed portion are configured to be radiated outwardly.

6. The insert-storage intravenous drip moving seat as claimed in claim 1, wherein the first fixed portions and the second fixed portion are equidistantly disposed on the same radius distance of the main body.

* * * * *